(12) United States Patent
Dahmen et al.

(10) Patent No.: US 8,609,589 B2
(45) Date of Patent: Dec. 17, 2013

(54) FUNGICIDAL AGENT COMBINATIONS

(75) Inventors: Peter Dahmen, Neuss (DE); Ulrike Wachendorff-Neumann, Neuwied (DE); Rolf Pontzen, Leichlingen (DE); Wolfram Andersch, Bergisch Gladbach (DE); Lutz Aβmann, Langenfeld (DE)

(73) Assignee: Bayer CropScience, Monheim (DE)

( * ) Notice: Subject to any disclaimer, the term of this patent is extended or adjusted under 35 U.S.C. 154(b) by 392 days.

(21) Appl. No.: 12/971,565

(22) Filed: Dec. 17, 2010

(65) Prior Publication Data

US 2011/0086888 A1  Apr. 14, 2011

Related U.S. Application Data

(66) Division of application No. 11/977,046, filed on Oct. 23, 2007, which is a division of application No. 10/565,175, Substitute for application No. PCT/EP2004/008073, filed on Jul. 20, 2004, now Pat. No. 7,309,711.

(30) Foreign Application Priority Data

Jul. 23, 2003  (DE) .................................. 103 33 371

(51) Int. Cl.
  *A01N 43/40*  (2006.01)
  *A01N 43/00*  (2006.01)
(52) U.S. Cl.
  USPC .......................................... 504/130; 504/139
(58) Field of Classification Search
  None
  See application file for complete search history.

(56) References Cited

U.S. PATENT DOCUMENTS

| | | | |
|---|---|---|---|
| 4,397,864 A | 8/1983 | Nakatani et al. | 424/282 |
| 4,570,005 A | 2/1986 | Nakatani et al. | 549/435 |
| 4,742,060 A | 5/1988 | Shiokawa et al. | 514/252 |
| 4,845,106 A | 7/1989 | Shiokawa et al. | 514/342 |
| 4,849,432 A | 7/1989 | Shiokawa et al. | 514/341 |
| 4,931,439 A | 6/1990 | Kristinsson | 514/242 |
| 4,996,325 A | 2/1991 | Kristinsson | 548/132 |
| 5,001,138 A | 3/1991 | Shiokawa et al. | 514/342 |
| 5,034,404 A | 7/1991 | Uneme et al. | 514/365 |
| 5,204,360 A | 4/1993 | Shiokawa et al. | 514/342 |
| 5,298,507 A | 3/1994 | Shiokawa et al. | 514/256 |
| 5,362,634 A | 11/1994 | Boeck et al. | 435/76 |
| 5,428,032 A | 6/1995 | Shiokawa et al. | 514/226.8 |
| 5,434,181 A | 7/1995 | Kodaka et al. | 514/471 |
| 5,461,167 A | 10/1995 | Shiokawa et al. | 548/202 |
| 5,489,603 A | 2/1996 | Uneme et al. | 514/365 |
| 5,496,965 A | 3/1996 | Boeck et al. | 536/7.1 |
| 5,532,365 A | 7/1996 | Kodaka et al. | 544/212 |
| 5,571,901 A | 11/1996 | Boeck et al. | 536/7.1 |
| 5,580,889 A | 12/1996 | Shiokawa et al. | 514/343 |
| 5,633,375 A | 5/1997 | Uneme et al. | 544/336 |
| 5,750,704 A | 5/1998 | Shiokawa et al. | 546/275.1 |
| 5,814,652 A | 9/1998 | Wu | 514/404 |
| 5,852,012 A | 12/1998 | Maienfisch et al. | 514/229.2 |
| 5,883,112 A | 3/1999 | Pilato et al. | 514/404 |
| 5,952,358 A * | 9/1999 | Meunier et al. | 514/357 |
| 6,015,910 A | 1/2000 | Wu | 548/367.7 |
| 6,022,871 A | 2/2000 | Maienfisch et al. | 514/229.2 |
| 6,022,967 A | 2/2000 | Shiokawa et al. | 544/298 |
| 6,277,791 B1 * | 8/2001 | Assmann et al. | 504/269 |
| 6,297,374 B1 | 10/2001 | Shiokawa et al. | 544/55 |
| 6,376,487 B1 | 4/2002 | Maienfisch et al. | 514/229.2 |
| 6,416,752 B1 * | 7/2002 | Richardson et al. | 424/84 |
| 6,627,753 B1 | 9/2003 | Maienfisch et al. | 544/67 |
| 2003/0232821 A1 | 12/2003 | Maienfisch et al. | 514/229.2 |

FOREIGN PATENT DOCUMENTS

| | | | |
|---|---|---|---|
| FR | 2806878 | * | 10/2001 |
| JP | 2003095832 | * | 4/2003 |
| WO | WO-9623411 | * | 8/1996 |
| WO | 99/24413 | | 5/1999 |
| WO | WO-9924413 | * | 5/1999 |
| WO | WO-02052940 | * | 7/2002 |
| WO | 03/015515 | | 2/2003 |
| WO | WO 03059067 | * | 7/2003 |

OTHER PUBLICATIONS

Pesticide Manual, 11th Edition, (month unavailable) No. 386, Editor, C.D.S. Tomlin, pp. 653-654, GY-81.
Pesticide Manual, 11th edition, (month unavailable) 1997, Editor: C.D.S. Tomlin, No. 109, "Carbofuran".
Pesticide Manual, 11th edition, (month unavailable) 1997, Editor: C.D.S. Tomlin, No. 110, "Carbosulfan".
Pesticide Manual, 11th edition, (month unavailable) 1997, Editor: C.D.S. Tomlin, No. 172, "Cycloprothrin".
Pesticide Manual, 11th edition, (month unavailable) 1997, Editor: C.D.S. Tomlin, No. 323, "Fipronil".
Pesticide Manual, 11th edition, (month unavailable) 1997, Editor: C.D.S. Tomlin, No. 376, "Furathiocarb".
Pesticide Manual, 11th edition, (month unavailable) 1997, Editor: C.D.S. Tomlin, No. 521, "Nitenpyram".
Pesticide Manual, 11th edition, (month unavailable) 1997, Editor, C.D.S. Tomlin, No. 5, "Acetamiprid".
Pesticide Manual, 11th edition, (month unavailable) 1997, Editor, C.D.S. Tomlin, No. 58, "Benfuracarb".
Pesticide Manual, 11th edition, (month unavailable) 1997, Editor, C.D.S. Tomlin, No. 113, "Cartap".
Pesticide Manual, 11th edition, (month unavailable) 1997, Editor, C.D.S. Tomlin, No. 650, "Silafluofen".

(Continued)

*Primary Examiner* — Alton Pryor

(57) ABSTRACT

The invention relates to novel fungicidally active compound combinations of 2'-cyano-3,4-dichloroisothiazole-5-carboxanilide of the formula

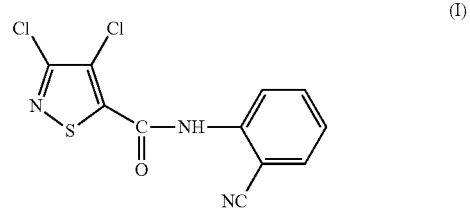

and active compounds listed in the disclosure.

8 Claims, No Drawings

(56) References Cited

OTHER PUBLICATIONS

Weeds, 15, (month unavailable) 1967, pp. 20-22, Harry R. Ungerer "Schiffsfarben—eine Spezialität der seenahen Lackindustrie".
Database WPI Section Ch, Week 199410 Derwent Publications Ltd., London, GB; AN 1994-077199 XP002305897 & JP 06 009313 A (Mitsui Toatsu Chem Inc) Jan. 18, 1994 Zusammenfassung.
Database Chemabs 'Online! Chemical Abstracts Service, Columbus, Ohio, US; XP002305896 gefunden im STN-International Database accession No. 126:15863 Zusammenfassung siehe IT: Registernummer 184106-82-9 & JP 08 245322 A (Mitsui Toatsu Chemicals) Sep. 24, 1996.
Database WPI, Section Ch, Week 199410, Derwent Publications Ltd., XP002305897 and JP06009313 A, Jan. 18, 1994.
Database Chemabs Online, Chemical Abstracts Service, XP002305896, Database accession No. 126:15863 and JP08245322 A, Sep. 24, 2996.
The International Search Report for PCT/EP2004/008073.

* cited by examiner

FUNGICIDAL AGENT COMBINATIONS

This application is a division of U.S. application Ser. No. 11/977,046, filed Oct. 23, 2007, which is a division of U.S. application Ser. No. 10/565,175, filed Jun. 1, 2006, now U.S. Pat. No. 7,309,711, issued Dec. 18, 2007, which was filed under 35 U.S.C. 371 as a national stage application of PCT/EP2004/008073, filed Jul. 20, 2004, which was published in German as International Patent Publication WO 2005/009131 on Feb. 3, 2005, and is entitled to the right of priority of German Patent Application 103 33 371.1, filed Jul. 23, 2003.

The present invention relates to novel active compound combinations which comprise the known 2'-cyano-3,4-dichloroisothiazole-5-carboxanilide on the one hand and other known insecticidally active compounds on the other hand, and which are highly suitable for controlling phytopathogenetic fungi.

It is already known that 2'-cyano-3,4-dichloroisothiazole-5-carboxanilide has fungicidal properties (cf. WO 99-024 413). The activity of this substance is good; however, at low application rates it is sometimes unsatisfactory.

Furthermore, it is already known that numerous neonicotinyls, carbamates, pyrethroids and phenylpyrazoles can be used for controlling insects (cf. EP-A 0 192 060, EP-A 0 580 553, Pesticide Manual, 11 th Edition (1997) No. 109, 110, 172, 323 and 376 and DE-A 196 53 417). The insecticidal activity of these substances is good; however, they do not have pronounced fungicidal activity.

It has now been found that the novel active compound combinations comprising 2'-cyano-3,4-dichloroisothiazole-5-carboxanilide of the formula (I)

and
(1) a neonicotinyl of the formula (II-a)

(imidacloprid)

(II-b)

(thiacloprid)

(II-c)

(thiamethoxam)

(II-d)

(clothianidin)

(II-e)

(nitenpyram)

(II-f)

(dinotefuran)

(II-g)

(acetamiprid)

and/or
(2) a carbamate of the formula (III)

in which the radicals $R^1$ and $R^2$ are as defined below:
(III-a) $R^1 =$ $$-S-N-CH_2-CH_2-CO-OCH_2-CH_3$$
$$\phantom{-S-N}|$$
$$\phantom{-S-N-}CH(CH_3)_2$$

$R^2$=$CH_3$
(benfuracarb)

(III-b) $R^1$=

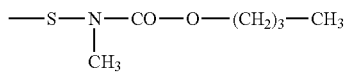

$R^2$=$CH_3$
(furathiocarb)

(III-c) $R^1$=$CH_3$
$R^2$=H
(carbofuran)

or (III-d) $R^1$=—S—N[$(CH_2)_3$—$CH_3$]$_2$
$R^2$=—$CH_3$
(carbosulfan)

and/or (3) a phenylpyrazole derivative of the formula

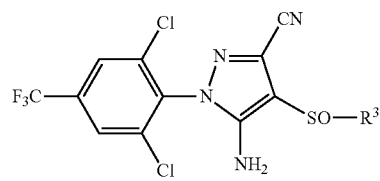

(IV)

in which the radical $R^3$ is as defined below:

(IV-a) $R^3$=—$CF_3$
(fipronil)

or (IV-b) $R^3$=$C_2H_5$
(ethiprole)

and/or (4) a pyrethroid of the formula

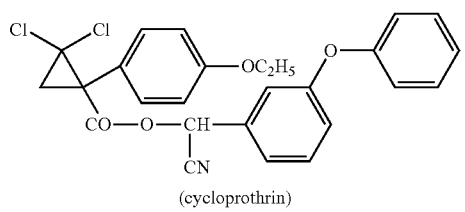

(V)

(cycloprothrin)

and/or (5) a pyrethroid derivative of the formula

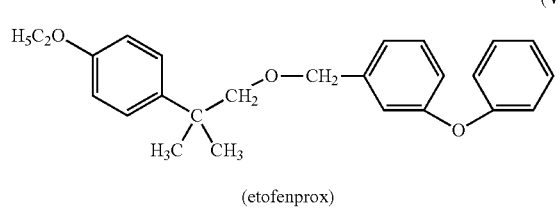

(VI-a)

(etofenprox)

or

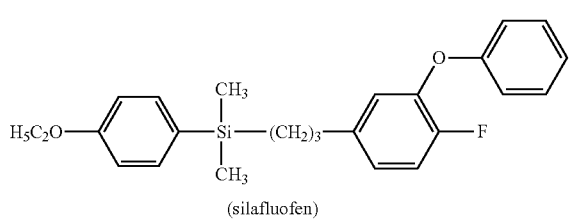

(VI-b)

(silafluofen)

and/or (6) the dithiol derivative of the formula

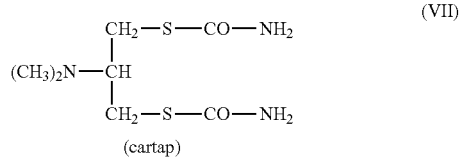

(VII)

(cartap)

and/or (7) the triazine derivative of the formula

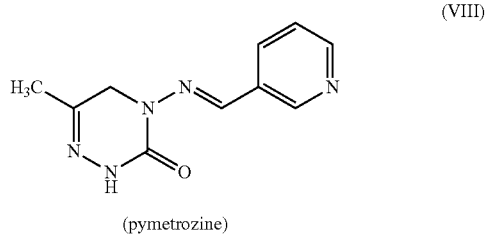

(VIII)

(pymetrozine)

and/or (8) the macrolide with the common name spinosad (IX) have very good fungicidal properties.

Surprisingly, the fungicidal activity of the active compound combinations according to the invention is considerably higher than the sum of the activities of the individual active compounds. Thus, an unforeseeable, true synergistic effect is present, and not just an addition of activities.

2'-Cyano-3,4-dichloroisothiazole-5-carboxanilide of the formula (I) is known (cf. WO 99-24 413).

The components present in addition to the active compound of the formula (I) in the active compound combinations according to the invention are likewise known. Specifically, the active compounds are described in the following publications:

(1) Compounds of the formulae (II-a) to (II-g)
EP-A 0 192 060
EP-A 0 235 725
EP-A 0 580 553
EP-A 0 376 279
Pesticide Manual, 11th Edition
(1997), No. 521
EP-A 0 649 845
Pesticide Manual, 11th Edition
(1997), No. 5

(2) Compounds of the formulae (IIIa) to (III-d)
Pesticide Manual, 11th Edition
(1997), Nr. 58, No. 376, Nr. 109
and No. 110

(3) Compounds of the formulae (IVa) and (IV-b)
Pesticide Manual, 11th Edition
(1997), No. 323
DE-A 196 53 417
(4) Compound of the formula (V)
Pesticide Manual, 11th Edition
(1997), No. 172
(5) Compounds of the formulae (VI-a) and (VI-b)
DE-A 3 117 510
Pesticide Manual, 11th Edition
(1997), No. 650
(6) Compound of the formula (VII)
Pesticide Manual, 11 th Edition
(1997), No. 113
(7) Compound of the formula (VIII)
EP-A 0 314 615
(8) Compound (IX)
EP-A 0 375 316

In addition to the activity of the formula (I), the active compound combinations according to the invention comprise at least one active compound of the compounds from groups (1) to (8). In addition, they may also comprise further fungicidally or insecticidally active additives.

The synergistic effect is particularly pronounced when the active compounds in the active compound combinations according to the invention are present in certain weight ratios. However, the weight ratios of the active compounds in the active compound combinations can be varied within a relatively wide range. In general, from 0.1 to 100 parts by weight, preferably from 0.1 to 50 parts by weight, of active compound of group (1), from 1 to 500 parts by weight, preferably from 10 to 100 parts by weight, of active compound of group (2), from 0.5 to 50 parts by weight, preferably from 1 to 20 parts by weight, of active compound of group (3), from 0.5 to 50 parts by weight, preferably from 1 to 20 parts by weight, of active compound of group (4), from 0.5 to 50 parts by weight, preferably from 5 to 20 parts by weight, of active compound of group (5), from 1 to 500 parts by weight, preferably from 2 to 20 parts by weight, of active compound of group (6), from 1 to 100 parts by weight, preferably from 1 to 30 parts by weight, of active compound of group (7), from 0.5 to 50 parts by weight, preferably from 1 to 20 parts by weight, of active compound of group (8)

are present per part by weight of active compound of the formula (I).

The active compound combinations according to the invention have very good fungicidal properties and can be employed for controlling phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for controlling cereal and rice diseases, such as *Pyricularia, Cochliobolus, Leptosphaeria, Rhizoctonia, Septoria, Pyrenophora, Pseudocercosporella, Erysiphe, Puccinia* and *Fusarium*, and for controlling diseases encountered in viticulture, such as *Uncinula, Plasmopara* and *Botrytis*, and furthermore in dicotyledonous crops for controlling powdery and downy mildew fungi and causative organisms of leaf spot.

The fact that the active compound combinations are well tolerated by plants at the concentrations required for controlling plant diseases permits the treatment of above-ground parts of plants, of propagation stock and seeds, and of the soil.

The active compound combinations according to the invention can be employed for foliar application or else as seed dressings.

The active compound combinations according to the invention can be converted to the customary formulations, such as solutions, emulsions, suspensions, powders, foams, pastes, granules, aerosols, microencapsulations in polymeric substances and into coating compositions for seed, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Suitable liquid solvents include, essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, and natural and synthetic polymers in the form of powders, granules or latices, such as gum arabic, polyvinyl alcohol and polyvinyl acetate, or else natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compounds, preferably between 0.5 and 90%.

The compounds (I) and (II) can be applied together, that is jointly or separately, or in succession, the sequence in the case of separate application generally not having any effect on the control results.

In the formulations, the active compound combinations according to the invention can be present as a mixture with other known active compounds such as fungicides, insecticides, acaricides and herbicides, and as mixtures with fertilizers or plant growth regulators.

Examples of suitable mixing components are the following compounds:

Fungicides:

2-phenylphenol; 8-hydroxyquinoline sulphate; acibenzolar-S-methyl; actinovate; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; boscalid; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; cis-1-(4-chlorophenyl)-2-(1H-1,2,4-triazol-1-yl)cycloheptanol; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; methyl 1-(2,3-dihydro-2,2-dimethyl-1H-inden-1-yl)-1H-imidazole-5-carboxylate; methyl 2-[[[cyclopropyl[(4-methoxyphenyl)imino]methyl]thio]methyl]-.alpha.-(methoxymethylene)benzeneacetate; methyl 2-[2-[3-(4-chlorophenyl)-1-methyl-allylideneaminooxymethyl]phenyl]-3-methoxyacrylate; metiram; metominostrobin; metrafenone; metsulfovax; mildiomycin; monopotassium carbonate; myclobutanil; myclozolin; N-(3-ethyl-3,5,5-trimethylcyclohexyl)-3-formylamino-2-hydroxy benzamide; N-(6-methoxy-3-pyridinyl)cyclopropane-carboxamide; N-butyl-8-(1,1-dimethylethyl)-1-oxaspiro[4.5]decan-3-amine; natamycin; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; penthiopyrad; phosdiphen; phthalide; picobenzamid; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; silthiofam; simeconazole; sodium tetrathiocarbonate; spiroxamine; sulphur; tebuconazole; tecloftalam; tecnazene; tetcyclacis; tetraconazole; thiabendazole; thicyofen; thifluzamide; thiophanate-methyl; thiram; tiadinil; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide (2S)—N-[2-[4-[[3-(4-chlorophenyl)-2-propynyl]oxy]-3-methoxyphenyl]-ethyl]-3-methyl-2-[(methylsulphonyl)amino]-butanamide; 1-(1-naphthalenyl)-1H-pyrrole-2,5-dione; 2,3,5,6-tetrachloro-4-(methylsulphonyl)pyridine; 2,4-dihydro-5-methoxy-2-methyl-4-[[[[1-[3-(trifluoromethyl)phenyl]ethylidene]amino]oxy]methyl]phenyl]-3H-1,2,3-triazol-3-one; 2-amino-4-methyl-N-phenyl-5-thiazolecarbox-amide; 2-chloro-N-(2,3-dihydro-1,1,3-trimethyl-1H-inden-4-yl)-3-pyridinecarbox-amide; 3,4,5-trichloro-2,6-pyridinedicarbonitrile; 3-[(3-bromo-6-fluoro-2-methyl-1H-indol-1-yl)sulphonyl]-N,N-dimethyl-1H-1,2,4-triazole-1-sulphonamide;

And also copper salts and copper preparations, such as Bordeaux mixture; copper hydroxide; copper naphthenate; copper oxychloride; copper sulphate; cufraneb; copper(I) oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, teclof-talam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbophenothion, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothiazoben, codlemone, coumaphos, cyanofenphos, cyanophos, cycloprene, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflu-benzuron, dimethoate, dimethylvinphos, dinobuton, dinocap, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethion, ethoprophos, etoxazole, etrimfos, famphur, fenamiphos, fenazaquin, fenbutatin oxide, fenfluthrin, fenitrothion, fenobu-carb, fenothiocarb, fenoxacrim, fenoxycarb, fenpropathrin, fenpyrad, fenpyrithrin, fenpyroximate, fensulfothion, fenthion, fentrifanil, fenvalerate, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), gamma-HCH, gossyplure, grandlure, granulosis viruses, halfenprox, halofenozide, HCH, HCN-801, heptenophos, hexaflumuron, hexy-thiazox, hydramethylnone, hydroprene, IKA-2002, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae*, *Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]-octane-3-carbonitrile (CAS-Reg. No. 185982-80-3) and the corresponding 3-endo-isomer (CAS-Reg. No. 185984-60-5) (cf. WO-96/37494, WO-98/25923), and also preparations which comprise insecticidally active plant extracts, nematodes, fungi or viruses.

The active compound combinations can be used as such, in the form of their formulations or as the use forms prepared therefrom, such as ready-to-use solutions, emulsifiable concentrates, emulsions, suspensions, wettable powders, soluble powders and granules. They are used in the customary manner, for example by watering, spraying, atomizing, scattering, spreading, and as a powder for dry seed treatment, a solution for seed treatment, a water-soluble powder for seed treatment, a water-soluble powder for slurry treatment, or by encrusting.

When using the active compound combinations according to the invention, the application rates can be varied within a relatively wide range, depending on the kind of application. In the treatment of parts of plants, the application rates of active compound combination are generally between 0.1 and 10 000 g/ha, preferably between 10 and 1000 g/ha. In the treatment of seed, the application rates of active compound combination are generally between 0.001 and 50 g per kilogram of seed, preferably between 0.01 and 10 g per kilogram of seed. In the treatment of the soil, the application rates of active compound combination are generally between 0.1 and 10 000 g/ha, preferably between 1 and 5000 g/ha.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof, are treated. The term "parts" or "parts of plants" or "plant parts" has been explained above.

With particular preference, plants of the plant cultivars which are in each case commercially available or in use are treated according to the invention. Plant cultivars are to be understood as meaning plants having new properties (traits) and which have been obtained by conventional breeding, by mutagenesis or by recombinant DNA techniques. They can be cultivars, breeds, biotypes or genotypes.

Depending on the plant species or plant cultivars, their location and growth conditions (soils, climate, vegetation period, diet), the treatment according to the invention may also result in superadditive (synergistic) effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties (traits) to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIA, CryIIA, CryIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed and which will be developed and/or marketed in the future.

The plants listed can be treated in a particularly advantageous manner with the active compound combinations according to the invention. The preferred ranges stated above also apply to the treatment of these plants.

The good fungicidal activity of the active compound combinations according to the invention is evident from the examples below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated according to S. R. Colby ("Calculating Synergistic and Antagonistic Responses of Herbicide Combinations", Weeds 15, (1967), 20-22) as follows:
if
X is the efficacy when applying active compound A at an application rate of m g/ha,
Y is the efficacy when applying active compound B at an application rate of n g/ha, and
E is the efficacy when applying the active compounds A and B at application rates of m and n g/ha,
then $$E = X + Y - \frac{X \cdot Y}{100}.$$

The efficacy is calculated in %. 0% is an efficacy which corresponds to that of the control, while an efficacy of 100% means that no infection is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The examples that follow illustrate the invention.

EXAMPLES

Example 1

*Erysiphe*-Test (barley)/protective
Solvent: 50 parts by weight of dimethylformamide
Emulsifier: 1 part by weight of alkylaryl polyglycol ether To produce a suitable preparation of active compound, 1 part by weight of active compound or active compound combination is mixed with the stated amount of solvent and emulsifier, and the concentrate is diluted with water to the desired concentration, or a commercial formulation of active compound or active compound combination is diluted with water to the desired concentration.

To test for protective activity, young plants are sprayed with the preparation of active compound at the stated application rate.

1 day after the treatment, the plants are dusted with spores of *Erysiphe graminis* f. sp. *hordei*.

The plants are placed in the greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

Active compounds, application rates and test results are shown in the table below.

TABLE 1

Erysiphe-Test (barley)/protective

| Active compound | Active compound application rate in g/ha | Efficacy in % |
|---|---|---|
| Known: | 100 | 0 |
|  | 50 | 0 |

(I)

TABLE 1-continued

Erysiphe-Test (barley)/protective

| Active compound | Active compound application rate in g/ha | Efficacy in % |
|---|---|---|
| Known: | 100 | 0 |

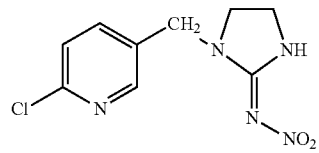

(II-a)

| According to the invention: | | calc.* | found |
|---|---|---|---|
| (I) | 100 | 0 | 26 |
| + | + | | |
| (II-a) | 100 | | |
| 1:1 | | | |

*Calculated using Colby's formula

What is claimed is:

1. A synergistic fungicidal composition comprising an active compound combination consisting of
   (a) 2'-cyano-3,4-dichloroisothiazole-5-carboxanilide of formula (I)

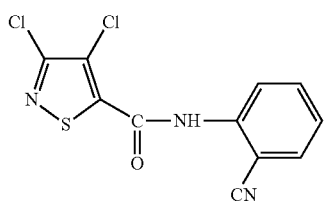

and (b) one or more of the compounds selected for active groups (1) a neonicotinyl of formula (II-b)

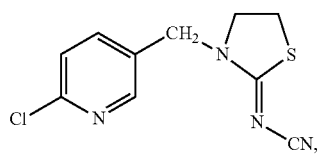

(thiacloprid)

and/or (2) a phenylpyrazole of formula (IV)

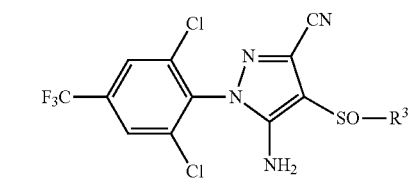

in which (i) for fipronil (formula IV-a), $R^3$ is —$CF_3$, or (ii) for ethiprole (formula IV-b), $R^3$ is $C_2H_5$, and (c) an extender or extenders and/or surfactants.

2. A composition according to claim 1 wherein in the active compound combinations the weight ratio of the active compound of formula (I) to active compound of group (1) is between 1:0.1 and 1:100, and/or active compound of group (2) is between 1:0.5 and 1:50.

3. A method for controlling fungi in viticulture and dicotyledonous crops comprising applying an effective amount of an active compound combination according to claim 1 to the fungi and/or their habitat.

4. A process for preparing a fungicidal composition according to claim 1 comprising mixing the active compound combination with an extender or extenders of the extenders and/or surfactants.

5. A composition according to claim 1, wherein component (b) is fipronil.

6. A composition according to claim 1, wherein the active compound combination consists of isotianil and thiacloprid.

7. A composition according to claim 1, wherein the active compound combination consists of isotianil and ethiprole.

8. A composition according to claim 1 wherein in the active compound combinations the weight ratio of the active compound of formula (I) to active compound of group (1) is between 1:0.1 and 1:50, and/or active compound of group (2) is between 1:1 and 1:20.

* * * * *